US012611276B2

(12) United States Patent
Spuhler et al.

(10) Patent No.: US 12,611,276 B2
(45) Date of Patent: Apr. 28, 2026

(54) CONTROL INTERFACE AND ROBOTIC SYSTEM COMPRISING SUCH A CONTROL INTERFACE

(71) Applicants: ACUSURGICAL, Montpellier (FR); CENTRE NATIONAL DE LA RECHERCHE SCIENTIFIQUE, Paris (FR); UNIVERSITE DE MONTPELLIER, Montpellier (FR)

(72) Inventors: Christoph Spuhler, Montpellier (FR); Yassine Haddab, Montpellier (FR); Philippe Poignet, Gignac (FR); Antoine Morel, Montpellier (FR); Alonso Sanchez, Juvignac (FR)

(73) Assignees: Acusurgical, Montpellier (FR); Centre National De La Recherche Scientifique, Paris (FR); Universite De Montpellier, Montpellier (FR)

( * ) Notice: Subject to any disclaimer, the term of this patent is extended or adjusted under 35 U.S.C. 154(b) by 463 days.

(21) Appl. No.: 17/997,360

(22) PCT Filed: Apr. 30, 2021

(86) PCT No.: PCT/EP2021/061439
§ 371 (c)(1),
(2) Date: Oct. 27, 2022

(87) PCT Pub. No.: WO2021/219863
PCT Pub. Date: Nov. 4, 2021

(65) Prior Publication Data
US 2023/0190399 A1 Jun. 22, 2023

(30) Foreign Application Priority Data
Apr. 30, 2020 (FR) ...................................... 2004321

(51) Int. Cl.
A61B 34/00 (2016.01)
A61B 34/37 (2016.01)
A61F 9/007 (2006.01)

(52) U.S. Cl.
CPC .............. *A61B 34/76* (2016.02); *A61B 34/37* (2016.02); *A61F 9/007* (2013.01)

(58) Field of Classification Search
CPC ......... A61B 34/30; A61B 34/37; A61B 34/70; A61B 34/75; A61B 34/77;
(Continued)

(56) References Cited

U.S. PATENT DOCUMENTS 6,063,095 A 5/2000 Wang et al.
9,579,088 B2 2/2017 Farritor et al.
(Continued)

OTHER PUBLICATIONS

International Search Report for PCT/EP2021/061439 (May 17, 2021).

*Primary Examiner* — Jon Eric C Morales
(74) *Attorney, Agent, or Firm* — ArentFox Schiff LLP

(57) ABSTRACT

A control interface (I) for a robotic system for the vitreo-retinal surgery includes a haptic device (1) equipped with an articulated chain (2) having a free end (3). The interface includes a guiding device (10). The guiding device (10) includes a stationary surface (11), a guiding (20) mounted on the stationary surface by a ball joint (21), and a rod (30) mounted on the guide (20) by a sliding connection (25) with an axis corresponding to that of the rod (30). The rod includes a first end (32) mounted stationary on the free end (3) of the haptic device (1) and a second end (33) on which a gripping member (5) is mountable.

12 Claims, 7 Drawing Sheets

(58) Field of Classification Search

CPC .............. A61B 17/00234; A61B 17/29; A61B 2090/372; A61B 34/25; A61B 34/35; A61B 34/74; A61B 34/76; A61B 90/37; A61B 1/06; A61B 1/3132; A61B 2017/00243; A61B 2017/00477; A61B 2017/00486; A61B 2017/1135; A61B 2017/291; A61B 2017/2919; A61B 2017/2927; A61B 2017/2929; A61B 2017/305; A61B 2034/302; A61B 2034/305; A61B 2034/715; A61B 2034/742; A61B 2090/373; A61B 2090/506; A61B 34/32; A61B 34/71; A61B 34/72; A61B 46/10; A61B 50/00; A61B 90/36; A61F 9/007; A61F 9/00727; B25J 13/02; B25J 13/025; B25J 13/04; B25J 17/0266; B25J 3/02; B25J 9/0048; B25J 9/1689; G05B 15/02; G09B 23/285; G16H 20/40; G16H 40/67

See application file for complete search history.

(56) References Cited

U.S. PATENT DOCUMENTS

| | | | | |
|---|---|---|---|---|
| 10,271,914 B2 | 4/2019 | Nambi et al. | | |
| 2012/0053701 A1 | 3/2012 | Yi et al. | | |
| 2015/0202009 A1* | 7/2015 | Nussbaumer | .......... | A61B 46/10 |
| | | | | 128/856 |
| 2018/0250086 A1* | 9/2018 | Grubbs | ................ | A61B 34/35 |
| 2019/0333635 A1 | 10/2019 | Beira et al. | | |

* cited by examiner

CONTROL INTERFACE AND ROBOTIC SYSTEM COMPRISING SUCH A CONTROL INTERFACE

This application is a National Stage Application of PCT/ EP2021/061439, filed Apr. 30, 2021, which claims benefit of Patent Application No. 2004321, filed Apr. 30, 2020 in France, and which applications are incorporated herein by reference. To the extent appropriate, a claim of priority is made to each of the above-disclosed applications.

TECHNICAL FIELD OF THE INVENTION

The invention relates to the field of the robotic platforms allowing for performing vitreoretinal surgery.

TECHNICAL BACKGROUND

The vitreoretinal surgery requires the insertion of surgical instruments into the eye of the patient. Classically, the surgical instruments are inserted at the level of the anterior portion of the eye of the patient using a hollow, pointed cylindrical rod referred to as a trocar. By inserting the instrument into the trocar, it passes through the sclera of the eye, then through the vitreous before reaching the posterior portion of the eye where the retina is located. The surgeon cannot do without the trocar. The latter contains a valve that prevents the fluid leakage while allowing the depth and the orientation of the tool in the eye to be varied easily. It is therefore a point of passage around which the surgeon performs movements with the instrument to position it appropriately on the retina.

The vitreoretinal surgeries require intervention on structures that may be only a few tens of micrometres in size. The surgeons have to be very dexterous, often in uncomfortable positions themselves. Some operations are even unfeasible, requiring capabilities beyond human limits.

The document U.S. Pat. No. 10,271,914 B2 discloses a robotic system 100 for the vitreoretinal surgery. The robotic system 100 comprises a robotic platform 126, to which a surgical instrument 114 is attached, and a haptic device 118 for manipulating the robotic platform 126. The robotic platform 126 comprises a terminal effector allowing to control the instrument in four or six degrees of freedom, the instrument being capable of performing at least translational movements and rotational movements about its axis. The haptic device 118 provides a positional feedback, allowing the surgeon to remotely control the movements of the robotic platform 126 using a stylus 122. There are no constraints on the movements that can be carry out with the stylus 122. Therefore, since in reality the instrument 114 is constrained by its passage through the trocar, certain actions performed by the surgeon with the stylus 122 are not possible.

The document U.S. Pat. No. 6,063,095 discloses a robotic system 10 comprising a robotic platform consisting of a set of robotic arms 26 to which surgical instruments are to be attached and a system for controlling the robotic platform. The control system comprises two control members 50, 52 allowing for remote control of the movements performed by 5 the robotic arms 26. The control members 50, 52 can be mounted either on a portable cabinet 54 or a support 900. In both cases, a set of joints JM1-JM5 allows translational and rotational movements of the control members 50, 52 about their respective axes as well as changes in their orientation. Each joint is associated with a position sensor (e.g. potentiometer) in order to determine the final position of the control members 50, 52. This 10 document does not disclose precisely how the position sensor data is treated to control the robotic arms 26. In any case, the control members 50, 52 are not linked to any haptic device.

In order to use these systems, the surgeon may need to be trained in articulated arm manipulations, which are very different in nature from those performed with a surgical instrument. In addition, the change from a conventional operation to one assisted by a robotic system can be confusing for the surgeon, who has to readjust each time he or she changes the operating mode.

SUMMARY OF THE INVENTION

The invention aims at overcoming the above-mentioned problems and to this end proposes a control interface for a robotic system for the vitreoretinal surgery comprising a haptic device equipped with an articulated chain having a free end, characterised in that it comprises a guiding device comprising:
  a stationary surface,
  a guiding means mounted on the stationary surface by a ball joint,
  a rod mounted on said guiding means by a sliding connection with an axis corresponding to that of the rod, said rod comprising a first end mounted stationary on the free end of the haptic device and a second end on which a gripping member is intended to be mounted.

When the surgeon uses the control interface according to the invention, he or she performs the same manipulations as if he or she were handling the surgical instrument itself. Indeed, when the surgeon manipulates the gripping member, the actions exerted on it are reproduced at the end of the chain by the surgical instrument.

In this respect, the arrangement of the rod in relation to the stationary surface plays a central role in the transmission of the movements performed by the gripping member. With the rod mounted on the guiding means by a sliding connection and the guiding means itself mounted on the stationary surface by a ball joint, the rod is constrained in the same way as an instrument is constrained by its passage through the trocar. Thus, its depression and orientation can be changed, but it will always be constrained to pass through a same point (the centre of the ball joint). Thus, in addition to depressing/retracting movements and the changes of orientation, the rotational movements of the rod around its axis can also be performed.

These movements of translation along the axis of the rod and rotation about the axis of the rod are then faithfully transmitted to the haptic device since the first end of the rod is stationary mounted on the free end of the haptic device. The haptic device is then able to measure them.

Of course, when reference is made to the surgical instrument, this refers to the various surgical instruments that may be used in vitreoretinal surgery.

According to various characteristics of the invention which may be taken together or separately:
  the control interface comprises said gripping member, the gripping member and the rod respectively comprising detection means adapted to detect a pressure exerted by a user on said gripping member,
  a first detection means is a magnet and a second detection means is a Hall-effect sensor,
  the gripping member comprises a deformable gripper and a movable portion on which said magnet is stationary mounted, said movable portion being able to displace when the gripper deforms, the rod is in the form of a hollow body internally delimiting a housing, said second detection means is arranged in the housing, the stationary surface comprises an opening and the guiding means comprises a spherical member and an adapting element for the spherical member in the opening, said opening, the adapting element and the spherical member forming the ball joint, the rod is cylindrical in shape, the spherical member being hollow and having a plain bearing that matches the shape of the rod so as to form the sliding connection, the rod comprises supply means for the second detection means arranged in the housing, said supply means being electrically connected to the second detection means and capable of receiving an electrical signal emitted by the second detection means when a pressure is exerted by a user on said gripping member, the guiding device comprises a rotating collector arranged coaxially around the rod, said collector comprising an inner ring attached to the rod and an outer ring attached to an axle of the articulated chain on which the free end of the haptic device is located, the control interface comprises a sterile cover interposed between the gripping member and the second end of the rod.

The invention further relates to a robotic system for the vitreoretinal surgery comprising:

a robotic platform comprising at least one robotic arm intended for carrying at least one surgical instrument, said robotic arm comprising an actuation module comprising at least one actuator, a console comprising a control interface as described above, a treatment module connected to the control interface and to the actuation module by a communication network, said treatment module comprising at least one processor, a memory and a software for analysing the measurements performed by the haptic device and for calculating and giving movement setpoints to the robotic arm, said platform being configured so that the movements applied to the rod are reproduced on said surgical instrument by means of the robotic arm.

Preferably, the robotic system is configured so that the pressures exerted on the gripping member and the movements that are applied to it are reproduced by the surgical instrument by means of the robotic arm.

BRIEF DESCRIPTION OF THE FIGURES

Further objects, characteristics and advantages of the invention will become clearer in the following description, made with reference to the attached figures, in which.

DETAILED DESCRIPTION OF THE INVENTION

Figure 1:
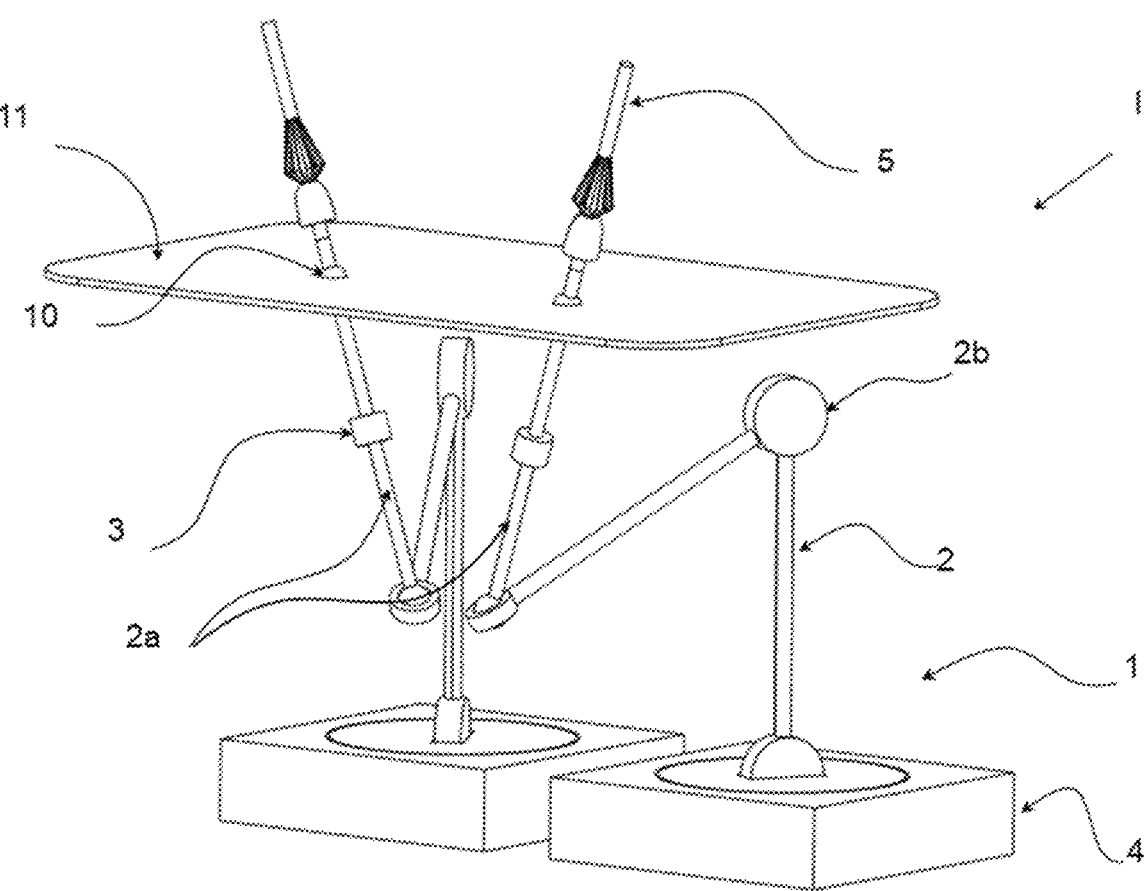
FIG. 1 shows a perspective view of a control interface according to the invention.

With reference to FIG. 1, the invention relates to a control interface I of a robotic system SR for the vitreoretinal surgery.

The robotic system SR in question is intended to be used by a practitioner, in particular by a surgeon in the context of a vitreoretinal surgery operation (only its control interfaces are illustrated in the example of embodiment shown in FIG. 1). It comprises a robotic platform PR comprising at least one robotic arm BR for manipulating a surgical instrument. Preferably, the robotic platform PR comprises two robotic arms BR, allowing the simultaneous manipulation of at least two surgical instruments. In addition, each of the robotic arms BR may comprise a module for actuating said robotic arm BR. This actuation module comprises a number of actuators adapted to the control of the robotic arm.

Furthermore, the robotic system SR comprises at least one control interface I associated with the robotic arm BR, it being understood that if the robotic platform PR comprises two robotic arms, the robotic system SR comprises at least one control interface, preferably two control interfaces I, each control interface I being associated with a robotic arm BR. In the example of embodiment shown in FIG. 1, the robotic system SR comprises two control interfaces I.

In addition, the robotic system SR comprises a treatment module MT capable of receiving and treating the measurement data received by the control interface or interfaces I so as to generate a movement of the surgical instrument as a function of the movements operated with the control interface or interfaces. This treatment module will be described in more detail in the description relating to FIG. 7.

The surgical instrument is any surgical instrument that may be used in vitreoretinal surgery. It goes without saying that the instrument is suitable for passing through a trocar. By way of background, the trocar is a hollow, pointed cylindrical rod that extends along a longitudinal axis. The instrument is not only capable of passing through the trocar, but also capable, optionally or in combination, of cutting, cauterising, injecting, aspirating, etc. In this respect, the practitioner is usually required to perform a pinch to operate the instrument, i.e. he/she performs the pinch gesture to make the instrument cut, cauterise, inject, aspirate, etc. In the following, the movements of the surgical instrument are described in relation to the longitudinal axis of the trocar.

The control interface I comprises a haptic device 1, a guiding device 10 and, advantageously, a gripping member 5 which is detachably mounted on the guiding device.

The haptic device 1 is a force-feedback device that allows for highly precise positioning measurements in the space. In other words, the purpose of the haptic device 1 is to measure the positions with a very high degree of faithful.

In this respect, it comprises an articulated chain 2 comprising a plurality of articulated arms 2*a* connected to each other by joints 2*b* designed so as to allow the articulated chain 2 to perform movements in all degrees of freedom.

The articulated chain comprises at least two articulated arms 2*a*. Each joint 2*b* is equipped with its own motor, which allows to create forces. Each joint 2*b* comprises its own angular position sensor which allows its position to be measured. One end of the articulated chain 2 is connected to a support 4, which is preferably stationary in relation to a console 60, which will be described in more detail in the description relating to FIG. 5*b*. A free end 3 of the articulated chain is, as will be seen in more detail below, attached to the guiding device 10. Thus, the haptic device 1 comprises all elements between the free end 3 and the support 4, comprising the free end 3 and the support 4.

The guiding device 10 comprises a stationary surface 11, a rod 30 and a guiding means 20 through which the surface 11 and the rod 30 cooperate.

The stationary surface 11 allows to ensure the maintaining of the guiding means 20, i.e. it provides the mechanical support. It is stationary in relation to the support 4 of the haptic device 1. In other words, there is no movement of the guiding device 10 relative to the haptic device 1. It is integrated into the aforementioned console 60 and is stationary in relation to the console 60.

In the example of embodiment shown in FIG. 1, the stationary surface 11 is planar. However, this is by no means limiting as the stationary surface 11 could also be of any other shape, for example, curved. What is important here is that the stationary surface 11 ensures the maintaining of the guiding means 20 while being stationary with respect to the support 4 of the haptic device 1.

As mentioned earlier, the rod 30 cooperates with the stationary surface 11 by means of the guiding means 20.

In this respect, the guiding means 20 is mounted on the stationary surface 11 by a ball joint 21 while the rod 30 is mounted on said guiding means 20 by a sliding connection 25 with an axis corresponding to that of the rod 30. By being arranged in this way in relation to each other, the rod 30, the guiding means 20 and the surface 11 form a sliding ball joint which will be described in more detail below.

Incidentally, the rod 30 of the guiding device can be manipulated in a change of orientation movement about the ball joint 21, in a rotational movement about the axis of the rod and in a translational movement with an axis corresponding to the axis of the rod. In this context, the rod 30 is from the point of view of the surgeon comparable to the rod of a surgical instrument used in the vitreoretinal surgery. The rotational movement of the rod 30 around its axis, i.e. the rotational movement of the rod 30 on itself, corresponds to a rotational movement of the instrument on itself. The movement of changing the orientation of the rod 30 corresponds to a change in the orientation of the instrument and the axis of the trocar in the eye of the patient, with the trocar necessarily following the changes in orientation of the surgical instrument. This is because the trocar is in a ball joint with the eye. Finally, the translational movement of the rod 30 along its axis corresponds to a depressing/retracting of the instrument into/from the trocar, the depression or the removal depending on the direction in which the translational movement is operated. That said, whatever the movement is operated, the rod 30 is always constrained to pass through a centre of the ball joint.

Figure 3:
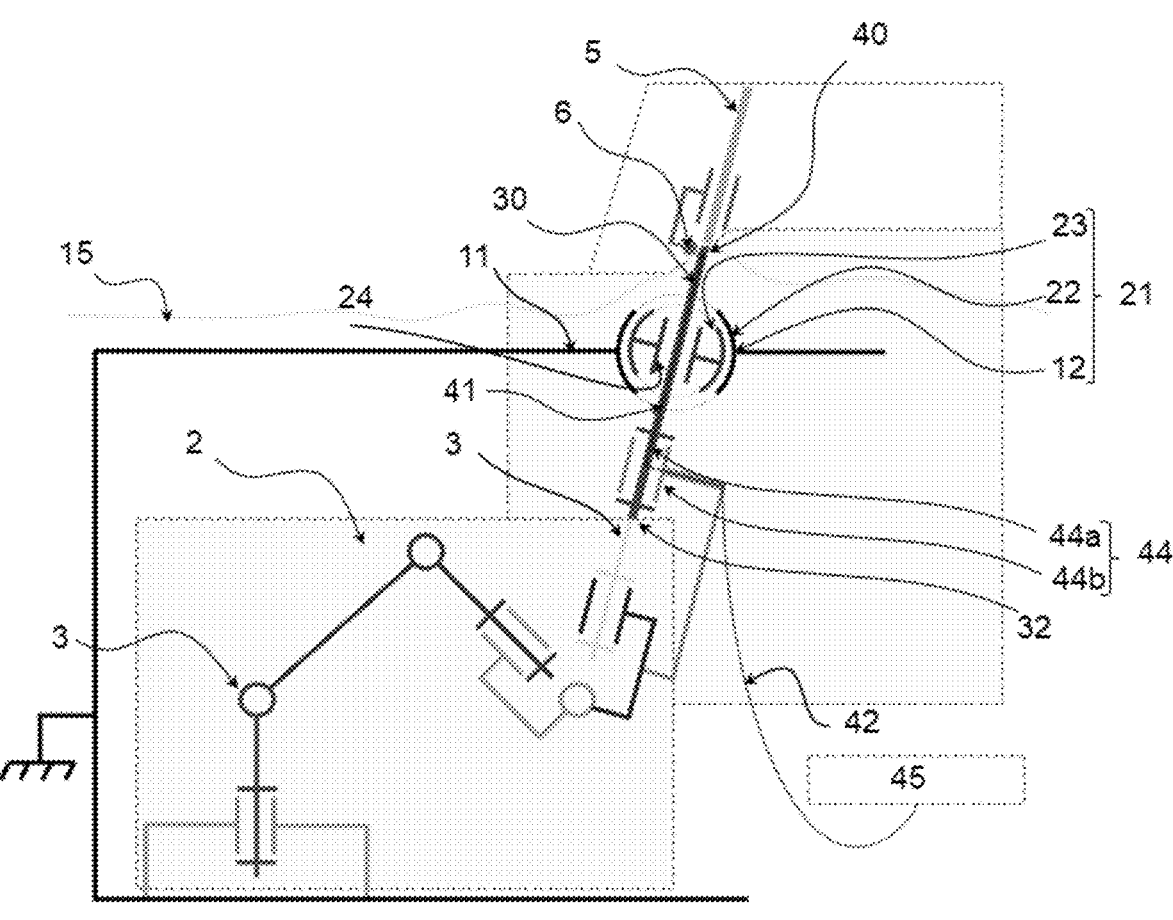
FIG. 3 is a schematic representation of the control interface according to the invention illustrating the various kinematic connections interconnecting the parts one to the other.

In addition, as can be better seen in FIG. 3, the rod 30 comprises a first end 32 stationary mounted on the free end 3 of the articulated chain of the haptic device. The guiding device 10 is therefore connected to the haptic device 1 via the first end 32 of the rod. As the first end 32 of the rod is stationary mounted on the free end 3 of the haptic device 1, the joints 3 of the articulated chain 2 adapt to the movements that are performed by the rod 30. These movements are measured in a precise manner and the data from these measurements are transmitted to the treatment module MT.

By manipulating the rod 30, the practitioner performs the same movements that he or she would have made if he or she had directly manipulated the instrument, while benefiting from the assistance provided by the robotic system SR.

Figure 4:
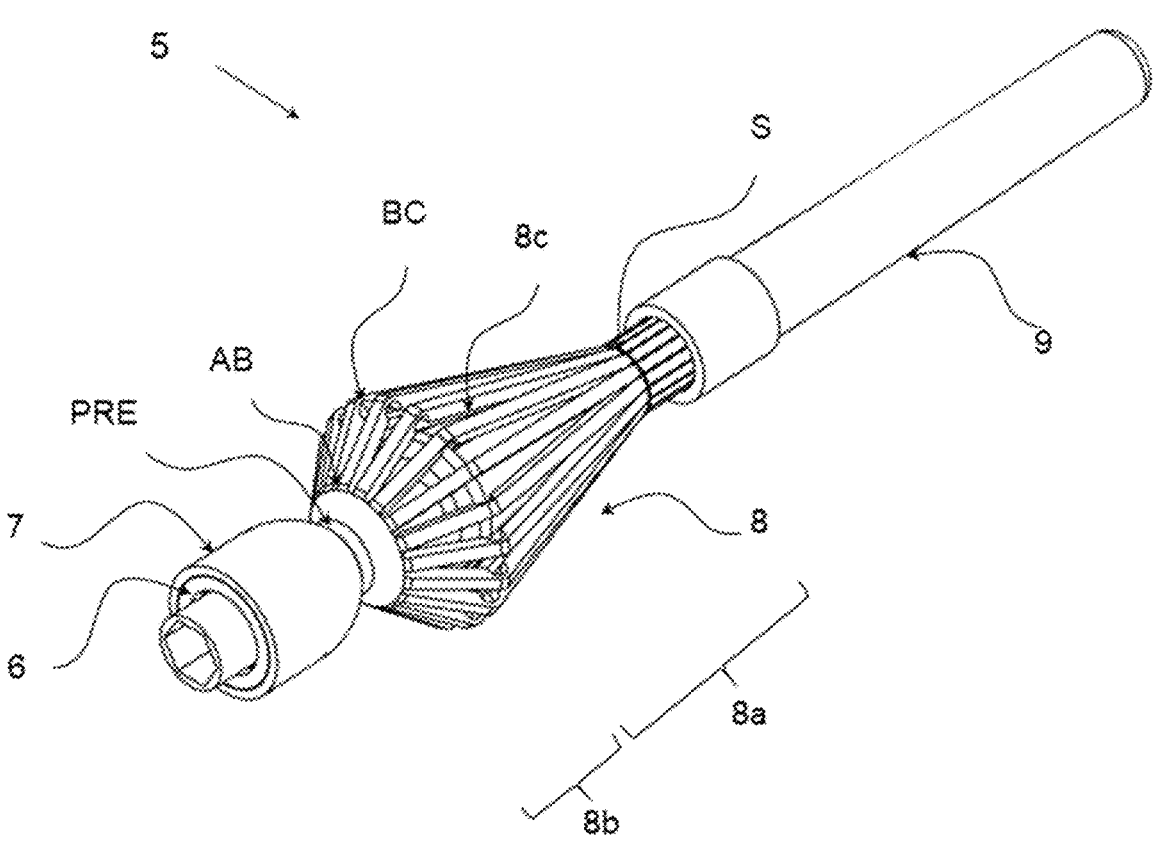
FIG. 4 illustrates a perspective view of a gripping member adapted for use in the control interface according to the invention.

However, in practice, the practitioner can advantageously control the movements of the rod 30 by means of a gripping member 5. The gripping member 5, which will be described in more detail in connection with the description of FIG. 4, is similar in shape to the surgical instrument, which makes the experience of the practitioner more faithful. In addition to having the same shape as a conventional surgical instrument, the gripping member 5 is also preferably sterile. The term "sterile" is used here in the medical sense and therefore implies that the gripping member 5 has been previously sterilised and is therefore germ-free.

Figure 2:
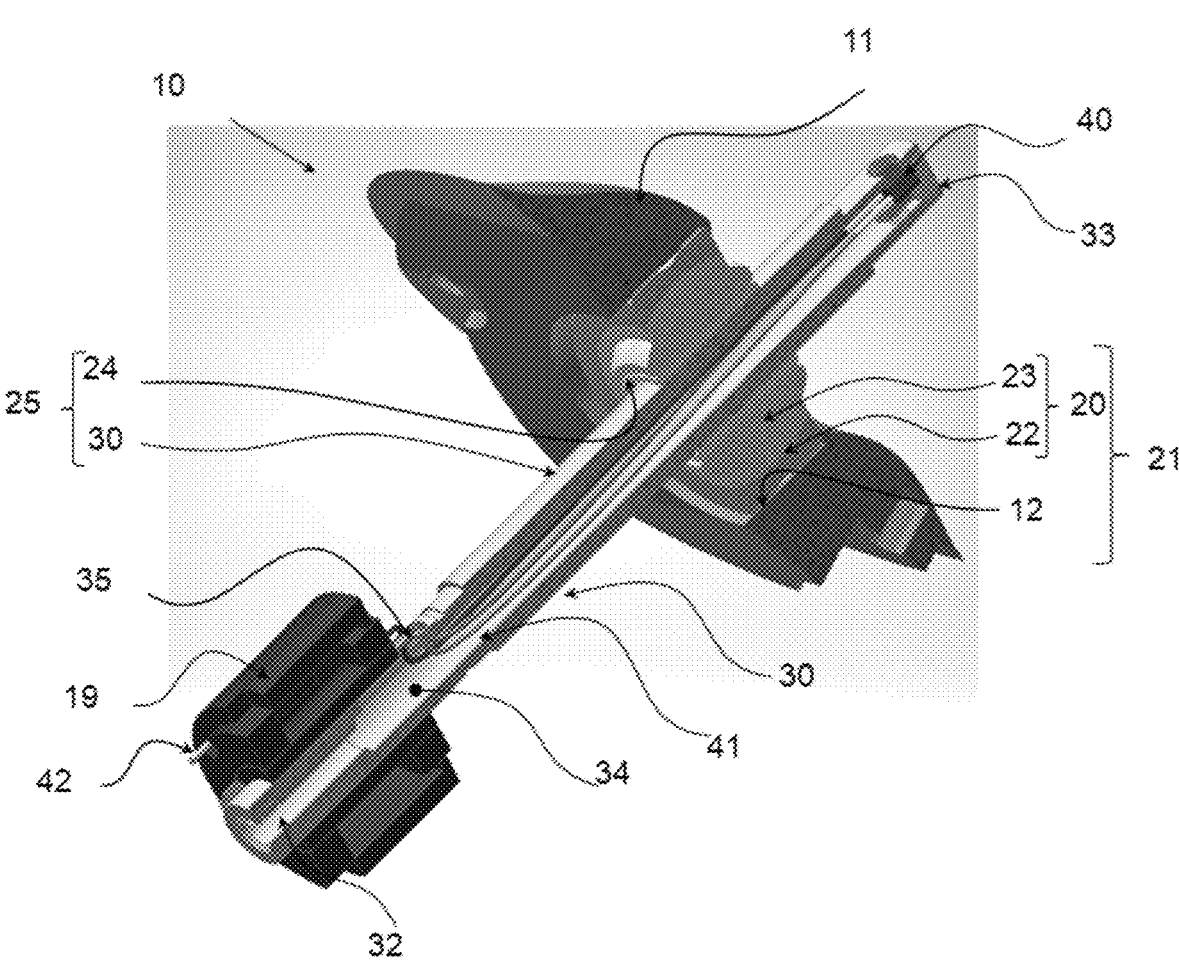
FIG. 2 shows a perspective cross-sectional view of a guiding device for the control interface according to the invention.

As illustrated in the example of embodiment shown in FIG. 2, the rod 30 comprises a second end 33 on which said gripping member 5 is intended to be mounted. The rod 30 is thus rigidly connected to the gripping member 5, which allows, when the gripping member 5 is present, to faithfully transmit the movements of said gripping member 5 to said rod 30 while allowing the surgeon to have sensations similar to those he or she would have when manipulating the surgical instrument.

With reference to FIG. 2, the arrangement of the rod 30 within the guiding device 10 and the operation of the guiding device 10 are more precisely described.

The stationary surface 11 comprises an opening 12 and the guiding means 20 comprises a spherical member 23 which co-operates with the opening 12 by means of an adapting element 22 to form the ball joint 21. The adapting element 22 is interposed between the opening 12 and the spherical member 23. It consists of a mechanical part comprising an outer ring of cylindrical shape and an inner housing of spherical shape in which the spherical member 23 moves freely. The dimensions of the adapting element 22 are chosen so that the adapting element externally matches the shape of the opening 12 and internally matches the shape of the spherical member 23. This configuration allows to vary the orientation of the rod 30, in particular because the spherical member 23 can move freely in the inner housing of the adapting element 22. In addition, it follows from this configuration that the centre of the ball joint 21 is the centre of the spherical member 23.

The above configuration is by no means limiting and the person skilled in the art may consider other configurations for designing the ball joint 21.

Preferably, the spherical member 23 is a chrome steel sphere.

In the example of embodiment shown in FIG. 2, the rod 30 is cylindrical in shape, while the spherical member 23 is hollow and has an inner part 24 that matches the shape of the rod 30 so as to form the sliding connection 25. For example, the inner part 24 may consist of a plain bearing made of Iglidur®. The inner part 24 therefore has cylindrical contours, the dimensions of which are chosen so that it adapts as snugly as possible around the rod 30 without preventing the rod 30 from sliding. Again, the configuration illustrated is by no means limiting. Alternatively, a rod 30 could be provided in the form of a straight block, the inner surface 24 would then have outlines in the form of a hollow block. There are many other ways of carrying out the sliding connection 25 between the spherical member 23 and the rod 30 which are within the reach of the person skilled in the art without, however, going beyond the inventive concept of the invention.

By combining the ball joint 21 and the sliding connection 25, a sliding ball joint is formed which allows the practitioner to mimic both retracting/depressing movements of the surgical instrument through the trocar, the changes in the orientation of the surgical instrument and the axis of the trocar, which as a reminder follows the movements of changes in orientation of the surgical instrument in the eye, and the rotational movements of the surgical instrument about that axis.

As further illustrated in FIG. 2, the rod 30 is advantageously in the form of a hollow body delimiting a housing 34 on the inside. In other words, the rod 30 itself is thus generally in the form of a hollow cylinder. The housing 34 thus formed advantageously allows to accommodate a second detection means 40 operating in synergy with a first detection means 6 comprised in the gripping member 5. The housing 34 also allows to accommodate supply means 41 for the second detection means 40. The relevance of said first and second detection means 6, 40 and supply means 41 is described below in the description relating to FIG. 4.

The supply means 41 of the second detection means 40 are preferably electrical wires. In order to prevent twisting the wires, i.e. to prevent the wires from becoming entangled, the guiding device 10 advantageously comprises a rotating collector 44 arranged coaxially around the rod 30. The rotating collector 44 allows the wires 41 to be electrically connected to an electronic board 45 whose role is to treat the data from the second detection means 40. More specifically, it allows the wires 41 located in the rod, which due to the sliding ball joint is rotatable, to be electrically connected to other wires 42 connected to the electronic board 45, which, unlike the rod 30, remains stationary with respect to the surface 11. In this regard, it should be noted that the rod 30 comprises an orifice 35 for the passage of the wires 41 from the housing 34 towards the collector 44.

Advantageously, the practitioner can perform multiple rotations of the rod 30, so to speak infinite rotations, without the wires 41 becoming tangled. In this respect, the collector 44 is itself a pivot connection. As schematically shown in FIG. 3, the collector 44 comprises an inner ring 44a attached to the rod 30 and an outer ring 44b attached to an axle of the articulated arm 2a on which the free end 3 of the haptic device is located. Means to prevent translation of the collector 44 relative to the rod 30 are also provided at the level of the rod. Such means may, for example, consist of protrusions arranged on an outer surface of the rod on either side of the collector 44. This allows to prevent the wires 41 from stretching and subsequently deteriorating.

With reference to the figures and in particular to FIGS. 1 and 4, the control interface I very advantageously comprises the gripping member 5. The use of the gripping member 5 has many advantages which will be better understood in the following.

The gripping member 5 is not permanently mounted on the guiding device 10. This is because it is detachably mounted on the guiding device 10. The manufacturer can therefore market the control interface I without the gripping member 5.

As shown in the example in FIG. 4, the gripping member 5 is in the form of a stylus similar in shape and size only to a standard instrument for the vitreoretinal surgery. The gripping member 5 is not a surgical instrument and is not intended to be used directly on the patient. It is a control instrument, i.e. it has a control function, in particular the control of the pinch. It works in cooperation with the rest of the control interface I to detect and measure the pinch.

The gripping member 5 comprises an elongated segment 9, a deformable gripper 8 and a movable portion 7 located side by side in this order.

The elongated segment 9, which is substantially cylindrical in shape, cooperates with the deformable gripper 8 to provide the practitioner with sensations in terms of touch that are equivalent to those he would have when manipulating a surgical instrument. In FIG. 4, only an outer envelope of the elongated segment 9 is visible, but this comprises an invisible core which extends well beyond the outer envelope and more precisely at least as far as the movable portion 7, as will be seen below.

The deformable gripper 8 has a diamond shape, i.e. a bi-pyramidal shape, in which the pyramids have a common base BC and in which one of the pyramids is truncated. The gripper 8 is thus formed by a complete pyramid 8a and a truncated pyramid 8b. The summit S of the complete pyramid is located on the side of the elongated segment 9, while the smaller base, hereinafter referred to as the "other base" AB, of the truncated pyramid is located near the movable portion 7. Each of the pyramids is formed by a plurality of tongues 8c which confers the gripper 8 its deformable character.

Furthermore, it should be noted that while the other base AB of the truncated pyramid 8b is rigidly connected to the movable portion 7 via a narrowed segment PRE, the other base AB and the movable portion 7 are movable relative to the elongated segment 9, in particular its core (not visible). Indeed, both the other base AB and the movable portion 7 are in sliding connection with the core of the elongated segment 9 which, although not distinguishable in FIG. 4, extends at least to the movable portion 7. This sliding connection, shown schematically in FIG. 3, is formed by an opening embodied in the other base AB and the movable portion 7, their respective openings being adjusted to the outer surface of the core of the elongated segment 9, i.e. they are suitably sized to form the sliding connection with the core of the elongated segment 9.

In such a configuration, when a pressure is exerted at the level of the common base BC, the tongues 8c being thinner at the level of the base BC compared to their thickness at the level of the summit S and the other base AB, the gripper 8 deforms, allowing the other base AB and the movable portion 7 to slide along the elongated segment 9 simultaneously. In this respect, the elongation of the gripper 8 can be changed depending on the pressure exerted and where this pressure is exerted on the gripper 8. At constant pressure, the closer the support is to the common base BC, the more the gripper 8 deforms and therefore lengthens. At the same time, for an identical support position between two manipulations, the higher the pressure exerted, i.e. the support rate, the more the gripper 8 deforms and therefore lengthens.

Figures 5A, 5B:
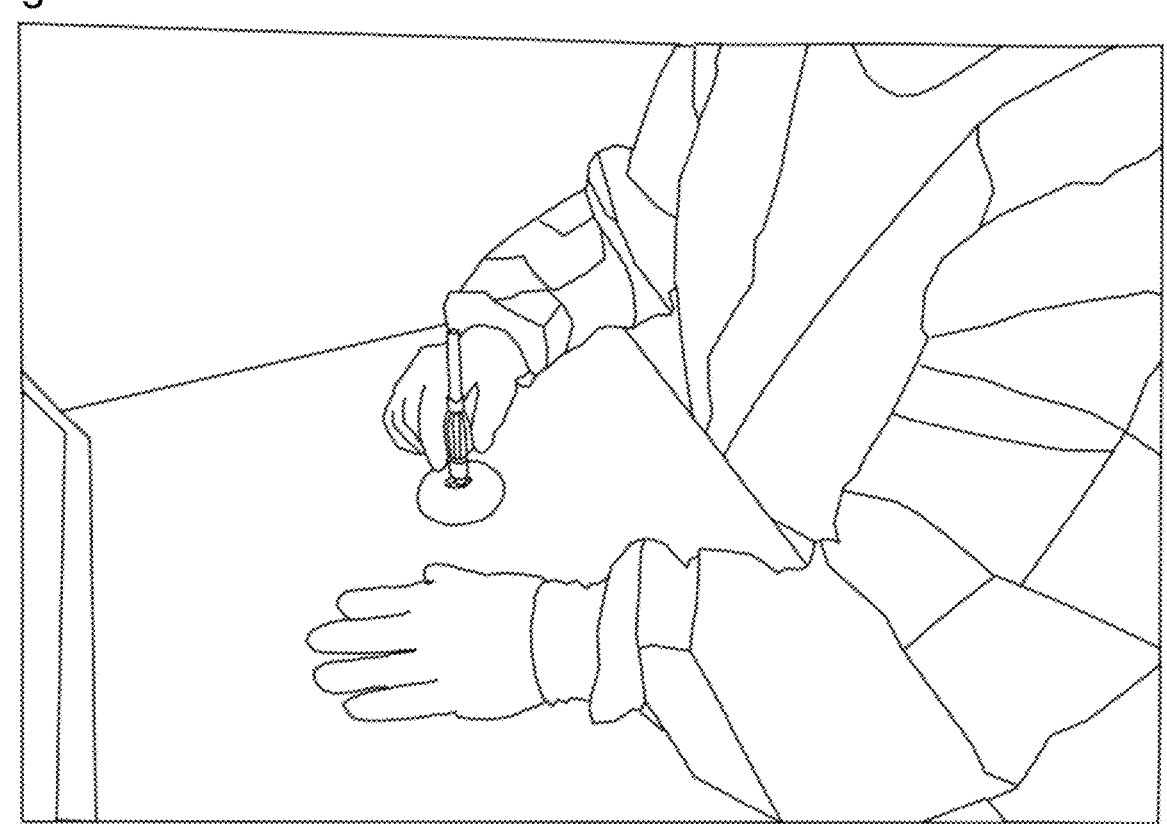
FIG. 5*a* shows a surgeon manipulating the gripping member.
FIG. 5*b* is a schematic representation of the control interface according to the invention, in particular equipped with an underhand mechanism.

The support position, i.e. the place where the pressure is exerted on the gripper 8, and the pressure exerted, i.e. the support rate, chosen therefore influence the displacement of the movable portion 7 and consequently, as will be seen in the following, the desired level of pinch. Thus, when the practitioner presses on the gripper 8, he can manipulate the gripping member 5 as he would manipulate the surgical instrument when he wants to perform a pinch and adapts the position of his/her fingers in relation to the common base BC according to the level of pinch he wants to obtain. FIG. 5a illustrates such a situation. The above configuration is only an example of the use of the gripping member 5. The person skilled in the art can envisage any other solution which allows to generate a displacement of the movable portion 7 when a pressure is exerted on the gripper 8.

This being said, if the gripping position and the support rate determine the desired pinch level, the way in which the elongation is detected and measured is explained in the following.

Very advantageously, the gripping member 5 comprises a detection means 6, hereinafter referred to as the first detection means 6, allowing for detecting the displacements of the movable portion 7. To this end, said first detection means 6 is stationary mounted on the movable portion 7 so that any displacement of the movable portion 7 along the core of the elongated segment 9 automatically induces a displacement of the first detection means 6. It should also be noted that once the gripping member 5 is mounted on the rod 30, the movable portion 7 also becomes movable with respect to the rod 30 and therefore with respect to the second detection means 40. This is important because it is the movements of the first detection means 6 that can be detected by the second detection means 40 of the guiding device 10 and subsequently measured by it. Thus, as soon as a sufficient pressure is exerted on the gripper 8 to cause the movable portion 7 and thus the first detection means 6 to displace, the displacement of the first detection means 6 can be measured by the second detection means 40. The first and second detection means 6, 40 thus operate in synergy to detect a pressure exerted on the gripping member 5. This is what confers the gripping member 5 its control function, in particular the control of the pinch performed by the practitioner.

Preferably, the first detection means 6 is a magnet and the second detection means 40 is a Hall-effect sensor. More precisely, the magnet is a permanent magnet. Thus, when sufficient pressure is exerted on the gripper 8 to cause the magnet 6 to displace, the magnetic field of the magnet displaces and thus varies in the eyes of the Hall-effect sensor 40, which as a reminder is located in the rod 30. The pressure rate can thus be deduced from the signal from the Hall-effect sensor.

The advantage of such a configuration compared to another detection system is that the gripping member 5 is thus devoid of electronics, the entire electronic portion being in the rod 30 and thus in the guiding device 10. It is therefore possible to detect the pressure applied to the gripping member 5, even if it has no electronics. In addition, the cost of the gripping member 5 can be kept low and it can therefore be more easily used as a consumable. This ensures that the required sterilisation conditions for the gripping member 5 are met at each operation. In addition, as the gripping member 5 is a consumable without electronics, it is easier to recycle.

Preferably, the Hall-effect sensor 40 is located at the level of said second end 33 in the housing 34 of the rod. This puts it as close as possible to the magnet 6, which enhances its ability to detect even the movements of said magnet even if they are with small amplitude. Of course, the Hall-effect sensor 40, as well as the magnet 6, can be arranged in any other way as long as a change in the pressure on the gripping member 5 can be detected. Advantageously, the housing 34 of the rod allows other types of sensors to be accommodated according to the additional functionalities that it is desired to confer on the control interface I according to the invention.

Moreover, while the combination of a magnet 6 with a Hall-effect sensor 40 has the above-mentioned advantages, other solutions can be envisaged to detect and measure the pressure of the practitioner on the gripping member 5. A Linear Variable Differential Transformer (LVDT) may be used. This type of sensor comprises a cylindrical transformer and a nucleus and has a response proportional to the displacement of the nucleus in the transformer. For example, a strain gauge may be used. The strain gauge allows the deformation of a part to be translated into a variation in electrical resistance. This being said, the person skilled in the art can use any sensor that allows to provide a position feedback.

The electrical signal SE from the Hall-effect sensor 40 is transmitted to the electronic board 45 via the wires 41, the collector 44 and the wires 42 for treating. The data of the sensor could be transmitted to the electronic board 45 by any other means known to the person skilled in the art. The data treated by the electronic board 45 is then transmitted to the treatment module MT which treats it and sends specific setpoints to the robotic platform PR so that the pressure exerted by the practitioner on the gripping member 5 can be reproduced on the surgical instrument by means of the robotic arm BR. The practitioner therefore does not need to learn any new gestures for the surgical instrument to perform a pinch as he manipulates the gripping member 5 in the same way as he would have manipulated the surgical instrument itself As illustrated in FIG. 5b, the control interface 1 may comprise a console 60. The console 60 consists of a desk, adjustable in height, in which the stationary surface 11, the guiding means 10 and the rod 30 are integrated according to the previously described configuration. It is at the level of the surface 11 that the console 60 is connected to the rest of the control interface I. In this respect, the stationary surface 11 may be integral with the console 60 or it may be a fitted part which is previously attached to the console 60. When the surgeon is seated at the level of the control interface I, as shown in FIG. 5a, the console 60 allows to provide the necessary support and stability to be able to manipulate the rod 30 and, if necessary, the gripping member 5. The console 60 forms a physical boundary between the surgeon and the haptic device 1 as the haptic device 1 is located below console 60.

Preferably, the console 60 has wrist rests (not shown) which the practitioner can lean on for stability. In addition, the console 60 may also comprise an underhand mechanism 62 adjustable in height. This underhand mechanism 62 can be placed under the gripping member 5 in order to facilitate the gripping of the latter while being adaptable to the morphology of the practitioner. The underhand mechanism 62 comprises at least one support surface 62a and a trunk 62b extending from the console 60. The height of the underhand mechanism 62 can be adjusted by carrying out a sliding connection between the trunk 62b and the console 60. Preferably the sliding connection is motorised, which allows the height of the underhand mechanism 62 to be adjusted according to the type of instrument used and the surgery carried out.

It should be noted, with reference to FIG. 3, that the control interface I may further comprise a sterile cover 15. The sterile cover 15 may be interposed between the gripping member 5 and the rest of the elements of the control interface I. This allows a sterile environment to be maintained from the second end 33 of the rod, where the gripping member 5 is mounted, to the patient. As such, the cover 15 is a constraint that must be taken into account when designing the control interface I. The sterile cover 15 preferably comprises sealing elements (not shown) between the two portions.

Figure 6:
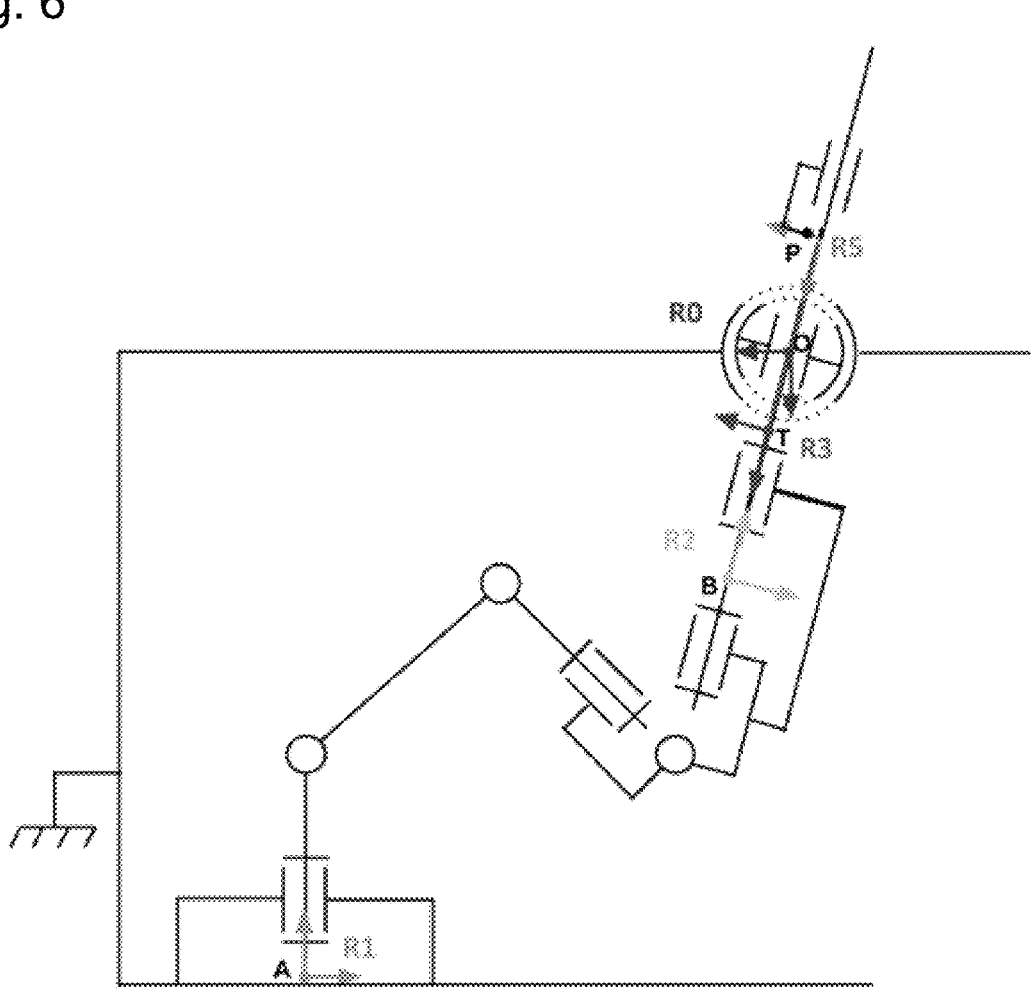
FIG. 6 is a schematic representation of the control interface according to the invention illustrating the mechanical connections in the guiding device.

With reference to FIG. 6, the kinematics and geometry of the guiding device 10 are described. A reference frame R0 with origin O is associated with the guiding means 20. A reference frame R1 with origin A is associated with the support 4 of the haptic device, which is preferably stationary with respect to the console 60. A reference frame R2 with origin B is associated with the free end 3 of the articulated chain of the haptic device. A reference frame R3 with origin T is associated with the rod 30. A reference frame R5 with origin P is associated with the elongated segment 9 of the gripping member 5.

The point T corresponds to a point on the rod 30 and the tip of the surgical instrument in the eye of the patient. The surgeon must therefore, in order to change the position of the tip of the surgical instrument, change the position of the point T in R0. To measure this position, an algorithm is implemented. This takes into account the geometric transformations between the reference frames R0 and R1, R1 and R2, R1 and R3 and R2 and R3. As mentioned earlier, the stationary surface 11 is stationary with respect to the support 4 of the haptic device 1, so the transformation between the reference frames R0 and R1 is constant and known by design. Similarly, as the free end 3 of the articulated chain is stationary relative to the first end 32 of the rod, the resulting geometric transformation between R2 and R3 is constant and known by design. The geometric transformation between the reference frames R1 and R2 is measured by the haptic device 1. The geometrical transformation between the reference frames R0 and R3 can be determined by calculations performed by the treatment module MT.

The point P of the reference frame R5 is linked to the movable portion 7. The position of the point P changes after a pressure is applied to the gripping member 5 and the gripper 8 is deformed from the position of the point P when no pressure is applied to the gripping member 5. As discussed earlier, this reflects the level of pinch that the practitioner would have exerted on the surgical instrument itself.

The measurement of the positions of these two points T and P allows to know all the actions that the practitioner wishes the surgical instrument, located at the end of the chain, to perform in the eye of the patient. These actions can be performed by the robotic platform PR in an identical or improved manner. It should be noted that measuring the position of the point T in the reference frame R0 alone would be sufficient to manipulate an instrument for which the pinch is not required, i.e. an instrument for which only the depression/the removal and the change of orientation are required. When a pinch is to be performed, the gripping member 5 becomes necessary to measure the pressure rate of the practitioner and it is then necessary to perform the measurement of the position of the point P in the reference frame R5.

In this respect, the options offered by the control interface I according to the invention are numerous. The ability of the haptic device 1 to generate forces allows to provide a feedback to the practitioner. Indeed, the haptic device 1 allows to:

limit the amplitude of the movement of the rod 30, possibly that of the gripping member 5, in order to force the instrument to remain in certain areas, limit the speed of displacement of the rod 30, and possibly that of the gripping member 5, in order to improve the precision and the stability of the movements, adapting the speed of the rod 30, and possibly that of the gripping member 5, to that of the robotic platform PR, for material and/or safety reasons, provide a haptic feedback based on forces measured by sensors located at the level of the instrument mounted on the robotic platform.

Figure 7:
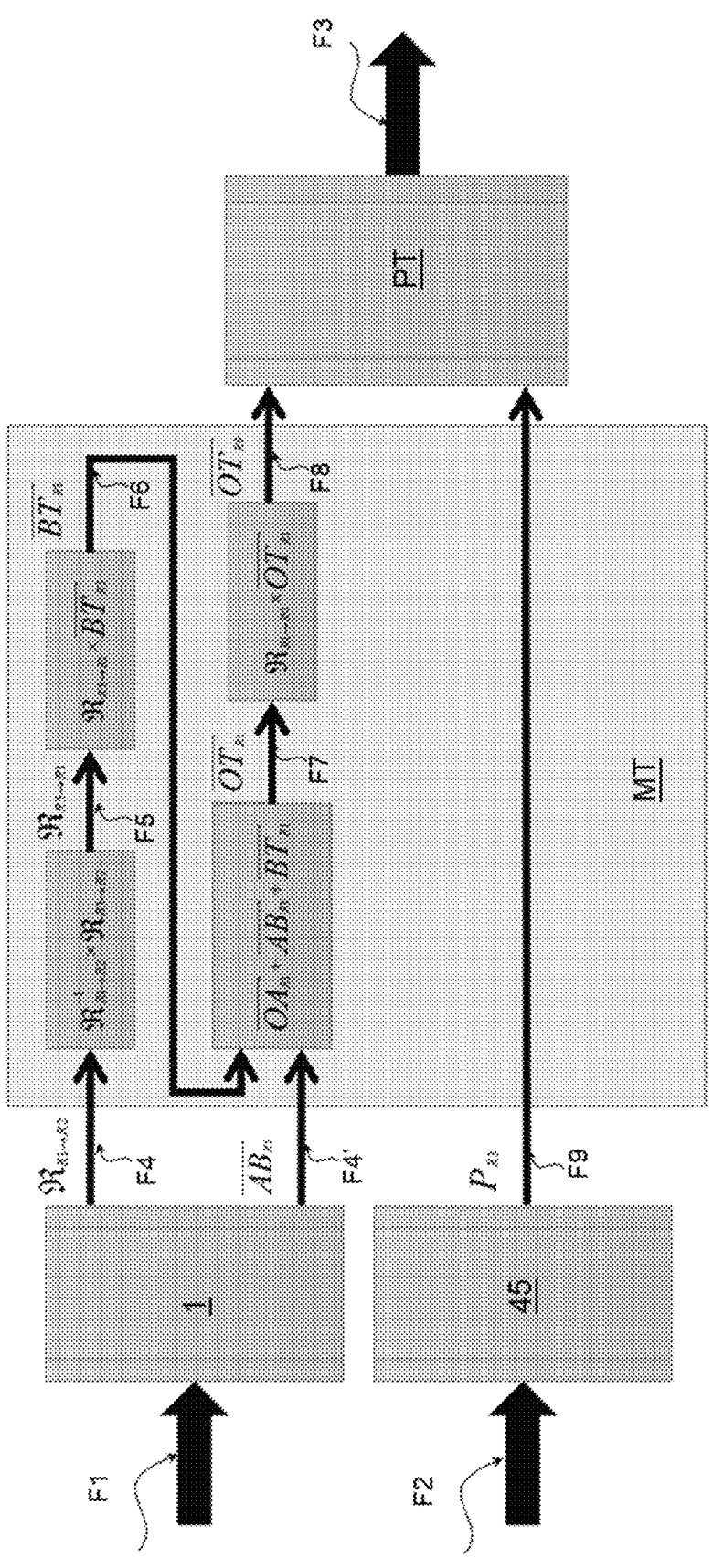
FIG. 7 is a schematic representation of the calculation and the data transmission between the control interface and the robotic platform.

In this respect, the transmission of data within the robotic system, as illustrated in FIG. 7, is in accordance with the method described below.

Advantageously, and as previously mentioned, the robotic system SR comprises a treatment module MT connected to the control interface I and the actuation module, as previously described, by a communication network (not illustrated). The treatment module is equipped with a processor and a memory. It can be any type of electronic or computer treatment means, for example a computer or any apparatus equipped with a processor and a memory, as long as it allows the treatment of the data received from the haptic device 1 and the electronic board 45.

The processor is configured to analyse and/or treat the data obtained from the haptic device 1 and the electronic board 45. In this respect, a treatment software can be installed on the processor in order to perform this treatment automatically and in real time. The software comprises spatial and kinematic geometry algorithms that allow the spatial configurations adopted by the rod 30 and possibly the gripping member 5 to be translated into setpoints for each of the actuators of the actuation module. These actuators act on the robotic platform PR to control the surgical instrument. As mentioned in the description of FIG. 7, the software determines the position of the point T in reference frame R0 and, if applicable, the position of the point P in the reference frame R5. These algorithms allow the instrument to respect its passage through the trocar. The algorithms advantageously allow to simplify the implementation of the additional options, seen above, which can be used by the practitioner by improving the initial gesture performed by the practitioner.

The memory allow to receive and store, even temporarily, the data transmitted and treated by the treatment module MT.

The arrow F1 indicates that the practitioner places the rod 30, and if applicable the gripping member 5, in a certain position and orientation, the arrow F2 indicates that the practitioner pinches the gripping member 5, when the control interface I comprises the latter, and the arrow F3 indicates that the surgical instrument is placed in the same position and orientation as the rod 30, if applicable the same position, orientation and pinch as the gripping member 5. Between the events F1, if necessary with F2, and the event F3, the transmission of the data is performed as follows:

1) The data measured by the haptic device 1 and the electronic board 45 are transmitted to the treatment module MT (arrows F4, F4' and F9), 2) The treatment module MT treats these data via the algorithms of the software and translates the configurations adopted by the rod 30 and possibly the gripping member 5 into setpoints for each of the actuators of the actuation module (processes between F4 and F8, between F4' and F8 and possibly F9), 3) The setpoints are sent to the actuation module, 4) The actuation module controls the robotic platform so that the surgical instrument reproduces the movements performed by the surgeon (arrow F3).

In the following, the process between F4 and F8 is described in more detail. Between F4 and F5, the treatment module MT has received the rotation that exists between the reference frames R1 and R2 (given by the haptic device 1). The treatment module MT inverts this and composes it with the rotation that exists between reference frames R3 and R2 (constant and known by design) to derive the rotation that exists between the reference frames R3 and R1. Between F5 and F6, the treatment module MT uses the rotation between the reference frames R3 and R1 and the expression of the vector BT in the reference frame R3 (constant and known by design) to derive the expression of the vector BT in the reference frame R1. Between F6 and F7, the treatment module MT receives the expression of the vector AB in the reference frame R1 (given by the haptic device 1) and adds it to that of the vector OA (constant and known by design) and to that of the vector BT (deduced after F6). He deduces the expression of the vector OT in the reference frame R1. Between F7 and F8, the treatment module uses the rotation that exist between the reference frames R1 and R0 (constant and known by design) and the expression of the vector OT in the reference frame R1 to derive the expression of the vector OT in the reference frame R0. This is exactly the data he needs to know what position and orientation the surgeon wants to give the instrument.

The invention claimed is:

1. A control interface for a robotic platform for vitreoretinal surgery comprising:
  a haptic device equipped with an articulated chain having a free end, and
  a guiding device comprising:
    a stationary surface,
    a guide mounted on the stationary surface by a ball joint,
    a rod mounted on said guide by a sliding connection with an axis corresponding to an axis of the rod, said rod comprising a first end mounted stationary on the free end of the haptic device and a second end on which a gripping member is mountable, wherein the guiding device is configured such that the rod is physically constrained to pass through a fixed point defined by the center of the ball joint.

2. The control interface according to claim 1, further comprising said gripping member, the gripping member and the rod respectively comprising detection means configured for detecting a pressure exerted by a user on said gripping member.

3. The control interface according to claim 2, wherein the detection means comprises a first and second detection means, wherein the first detection means is a magnet and the second detection means is a Hall-effect sensor, and wherein the gripping member is devoid of electronics.

4. The control interface according to claim 3, wherein the gripping member comprises a deformable gripper and a movable portion on which said magnet is mounted stationary, said movable portion displaceable when the gripper deforms.

5. The control interface according to claim 3, wherein the rod is a hollow body internally delimiting a housing, said second detection means being arranged in the housing.

6. The control interface according to claim 5, wherein the rod comprises supply means for the second detection means arranged in the housing, said supply means being electrically connected to the second detection means and adapted to receive an electrical signal emitted by the second detection means when a pressure is exerted by a user on said gripping member.

7. The control interface according to claim 2, further comprising a sterile cover interposed between the gripping member and the second end of the rod, and wherein the gripping member is detachable.

8. The control interface according to claim 1, wherein the stationary surface comprises an opening and the guide comprises a spherical member and an element for adapting the spherical member in the opening, said opening, the adapting element and said spherical member forming the ball joint.

9. The control interface according to claim 8, wherein the rod is cylindrical, the spherical member being hollow and having a plain bearing matching a shape of the rod to form the sliding connection.

10. The control interface according to claim 1, wherein the guiding device comprises a rotating collector arranged coaxially around the rod, said collector comprising an inner ring attached to the rod and an outer ring attached to an axle of the articulated chain on which the free end of the haptic device is located.

11. A robotic system for the vitreoretinal surgery comprising:
  a robotic platform comprising at least one robotic arm for carrying at least one surgical instrument, said robotic arm comprising an actuation module comprising at least one actuator,
    a console comprising a control interface for the robotic platform according to claim 1,
    a treatment module connected to the control interface and to the actuation module by a communication network, said treatment module comprising at least one processor, a memory and a software for analysing measurements performed by the haptic device and for calculating and giving movement setpoints to the robotic arm,
    said platform being configured so that movements applied to the rod are reproduced on said surgical instrument by the robotic arm.

12. The robotic system according to claim 11, wherein the control interface comprises said gripping member, the gripping member and the rod respectively comprising detection means configured for detecting a pressure exerted by a user on said gripping member, and wherein the robotic system is configured such that the pressures exerted on the gripping member and the movements which are applied to the gripping member are reproduced by the surgical instrument by the robotic arm.

* * * * *